United States Patent
Boghossian

(10) Patent No.: US 8,709,505 B2
(45) Date of Patent: Apr. 29, 2014

(54) THERAPEUTIC RINSE IN A SELF-HEATING PACKAGE

(75) Inventor: Juliet Agatha Boghossian, Glendale, CA (US)

(73) Assignee: Juliet Agatha Boghossian, Glendale, CA (US)

( * ) Notice: Subject to any disclaimer, the term of this patent is extended or adjusted under 35 U.S.C. 154(b) by 46 days.

(21) Appl. No.: 13/372,356

(22) Filed: Feb. 13, 2012

(65) Prior Publication Data

US 2012/0209177 A1    Aug. 16, 2012

Related U.S. Application Data

(60) Provisional application No. 61/442,717, filed on Feb. 14, 2011.

(51) Int. Cl.
- *A01N 65/00* (2009.01)
- *A61K 8/00* (2006.01)
- *A61F 7/12* (2006.01)

(52) U.S. Cl.
USPC ............... 424/725; 424/49; 604/78; 604/113

(58) Field of Classification Search
USPC .......... 601/15, 17; 604/78, 113; 424/49, 725, 424/736, 745, 760; 514/31
See application file for complete search history.

(56) References Cited

U.S. PATENT DOCUMENTS

| | | | |
|---|---|---|---|
| 5,626,022 A * | 5/1997 | Scudder et al. | 62/4 |
| 2003/0206942 A1* | 11/2003 | Kulkarni et al. | 424/443 |
| 2006/0073189 A1* | 4/2006 | Pinney et al. | 424/440 |
| 2007/0218114 A1* | 9/2007 | Duggan et al. | 424/443 |
| 2010/0152703 A1* | 6/2010 | Solomon | 604/514 |

OTHER PUBLICATIONS

Health911. Sore Throat. Aug. 14, 2010: http://web.archive.org/web/20100814232301/http://www.health911.com/sore-throat.*

* cited by examiner

*Primary Examiner* — Nicholas Lucchesi
*Assistant Examiner* — Leah Stohr
(74) *Attorney, Agent, or Firm* — Steptoe & Johnson LLP

(57) ABSTRACT

A therapeutic rinse for treating a sore throat including a self heating container having a reservoir. The self heating container is capable of reaching a temperature of at least 130 degrees Fahrenheit when activated. The therapeutic rinse includes a liquid composition having sodium chloride, water, an antibiotic, and a variety of vitamins, minerals and herbs stored in the reservoir of the self heating container. During use, the self heating container is activated and the liquid composition is heated inside the reservoir to about 130 degrees Fahrenheit.

20 Claims, 1 Drawing Sheet

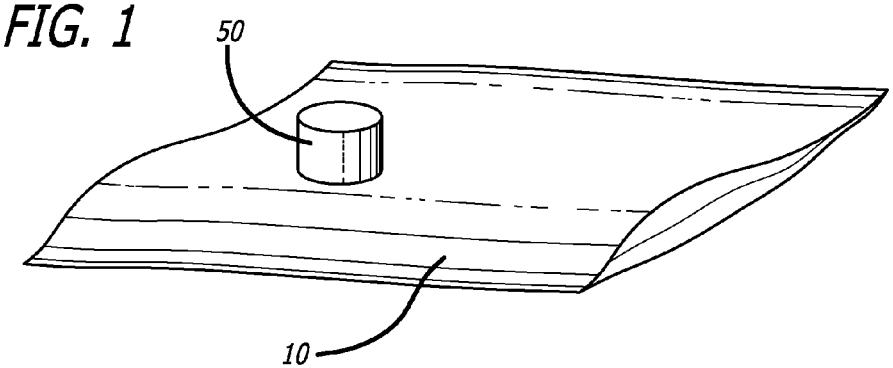
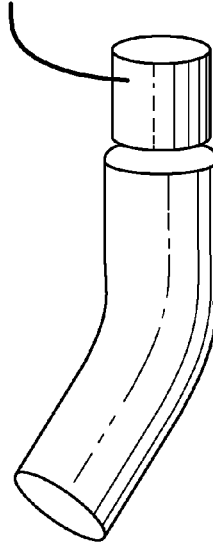
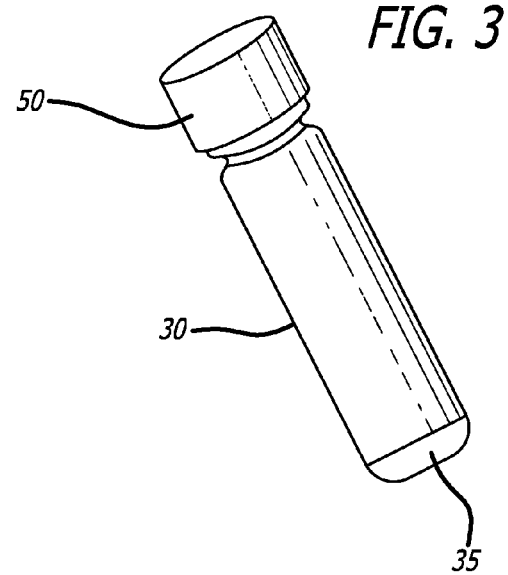
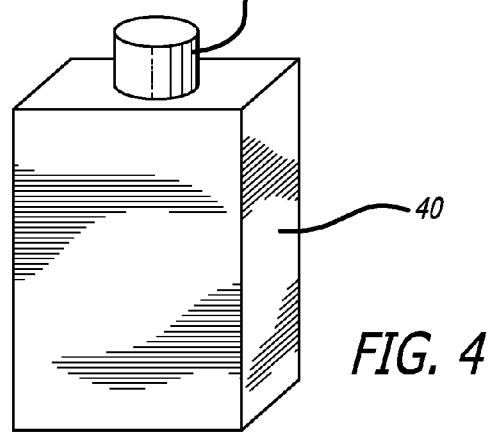

THERAPEUTIC RINSE IN A SELF-HEATING PACKAGE

CROSS REFERENCES TO RELATED APPLICATIONS

This application claims the benefit of U.S. Application Ser. No. 61/442,717, filed Feb. 14, 2011, the entire disclosure of which is expressly incorporated herein.

BACKGROUND

This invention relates to a therapeutic rinse in a self-heating package. More particularly, this invention relates to a self-heating package storing sodium chloride, water, a variety of vitamins, minerals and herbs ingredients and an antibiotic rinse mixture for treating sore throats, mouth sores and/or minor gum infections and or for use as a first aid disinfectant.

There are many home-remedies for treating the early signs of a sore throat, mouth sore and/or minor gum infection. However, these home-remedies are 1) not convenient when away from home, at work, at school, or traveling; 2) not as effective with one-to-two household ingredients; and 3) not consistent since the do-it-yourself home-made version can vary significantly. There are also commercially available products that suggest they can boost or support a person's immune system to help prevent illness, such as colds and sore throats. These home-remedies and commercially available products can be heated or mixed with hot water at home to provide a more soothing effect.

What is needed is an out-of-home and in-home remedy that is more convenient, effective and consistent. Specifically, 1) a therapeutic remedy that comes in a self-heating package that can be used by a person away from home; 2) a therapeutic remedy that is more comprehensive weakening bacteria then combating it with a complex mixture sodium chloride, vitamins, minerals, herbs ingredients and an antibiotic; and 3) a commercialized version of the do-it-yourself home remedy with proper measure and a complex mixture of vitamins, minerals, herbs ingredients and an antibiotic compacted into a dissolving tablet and/or powdered packet form.

SUMMARY

Briefly, and in general term, disclosed embodiments include a therapeutic rinse for treating a sore throat, mouth sore and/or minor gum infection including a self heating container having a reservoir. The self heating container is capable of reaching a temperature of at least 130 degrees Fahrenheit when activated. In use, the self heating container may reach between about 130 and 150 degrees Fahrenheit upon activation of the self heating container. In one embodiment, the self heating container includes a cap that measures an ounce of liquid.

The therapeutic rinse includes a liquid composition having sodium chloride, water, vitamins, minerals, herbs and an antibiotic stored in the reservoir of the self heating container. During use, the self heating container is activated and the liquid composition is heated inside the reservoir to about 130 degrees Fahrenheit.

In one embodiment, the liquid composition includes a ratio of about 7.5 mL of sodium chloride to about 180 ml of water. In another embodiment, the liquid composition includes a ratio of about 15 ml of sodium chloride to about 79 ml of water. Also, the liquid composition may include a total of about 180 mL (6 oz.) or about 90 ml (3 oz.). The liquid composition may include about 10 mg to about 100 mg of antibiotic. In other embodiments, the liquid composition may include about 20 mg to about 200 mg of antibiotic or about 15 mg to about 150 mg of antibiotic. The antibiotic selected may be either Zithromiacin, Cephalexin, or other upper respiratory antibiotics.

Embodiments are also directed to a method of forming a therapeutic rinse. The method may include preparing a liquid composition having sodium chloride, water, vitamins, minerals, herbs and an antibiotic. Further, the method includes a self heating container having a reservoir, wherein the self heating container is capable of reaching at least 130 degrees Fahrenheit. The liquid composition may be placed within the reservoir of the self heating container and the reservoir of the self heating container can be sealed with a cap or any tamper-proof device.

BRIEF DESCRIPTION OF THE DRAWINGS

FIG. 1 depicts a perspective view of one embodiment of a self-heating pouch including a therapeutic rinse;

FIG. 2 depicts a perspective view of one embodiment of a self-heating flexible tube stick including a therapeutic rinse;

FIG. 3 depicts a perspective view of one embodiment of a self-heating bottle including a therapeutic rinse; and FIG. 4 depicts a perspective view of one embodiment of a self-heating carton including a therapeutic rinse.

DETAILED DESCRIPTION

Turning now to the figures, which are provided by way of example and not limitation, the disclosed embodiment is a self-heating package that includes salt water, vitamins, minerals, herbs and an antibiotic rinse. Referring now to the drawings, wherein like reference numerals denote like or corresponding components throughout the drawings and, more particularly to FIGS. 1-4, there is shown different embodiments of a package for storing a therapeutic rinse.

As disclosed in more detail below, one embodiment is a therapeutic liquid or composition that can be used as a remedy for a sore throat, mouth sore and/or minor gum infection. In another embodiment, the therapeutic liquid or composition can be used to clean and disinfect minor scrapes and abrasions. In both of these embodiments, the therapeutic liquid is contained in a package that is self-heating. However, it has been contemplated that the therapeutic rinse can be stored in a regular container that is not self-heating. In this embodiment, users could self-heat the container or its contents if desired.

Therapeutic Rinse

The therapeutic rinse may be used to treat a viral or bacterial sore throat, mouth sore and/or minor gum infection. In one embodiment to treat and/or prevent a viral sore throat, commonly associated with the common cold, the therapeutic rinse has a liquid composition including a specific concentration of salt dissolved in water. In another embodiment the therapeutic rinse may be used to treat and/or prevent a bacterial infection, such as strep throat, and the therapeutic rinse may include a liquid composition including a concentration of salt and an antibiotic dissolved in water. Typically, signs of a bacterial infection consist of puss, green and/or yellow discharge. As used in this application, salt refers to sodium chloride. However, it has been contemplated that unrefined salt (sea salt), refined salt (table salt), and/or iodized salt can also be used. Also, water as used in this application can mean distilled water, filtered water or treated water.

One embodiment of a therapeutic rinse to treat a viral sore throat, mouth sore and/or minor gum irritation may include about 7.5 mL of salt to about 180 mL of water brought to a temperature of about 130 degrees Fahrenheit in a self-heating package or container. In another embodiment the therapeutic rinse may include about 15 mL of salt to about 79 mL of water. However, the temperature of the therapeutic rinse can range from 100 degrees Fahrenheit to about 150 degrees Fahrenheit. There is no medicinal treatment for a viral sore throat, only time and rest as a user's body fights the stages of what is known as the common cold. Therefore, there is no need for an antibiotic ingredient. However, if a user gargles with a high enough concentration of salt at the earliest sign of sore throat discomfort it can remedy a sore throat and greatly decrease the chances of getting the common cold; and if taken after the onset of a sore throat it can greatly decrease the duration/severity of the sore throat and common cold. Cells found in the mouth are made up of 70% water. These cells require water to function effectively. When high concentrations of salt are introduced to the mouth/throat, the water is extracted thereby isolating the virus and/or bacteria that is present and handicapping it from multiplying further. Water is essentially the fuel that feeds the cells, without it, the cells are compromised, and with it so is the virus. With repeated high concentration salt water rinses three times a day for a minimum two days viral cells can be eliminated remedying the sore throat. The subject therapeutic rinse consists of a high concentration of salt water in addition to a variety of vitamins and minerals to further combat the sore throat by introducing immunity building agents.

Bacterial cells that cause infections will be handicapped from multiplying when a high concentration of salt is introduced to the mouth/throat. A bacterial infection will also require an upper respiratory antibiotic rinse as well to combat the infection most effectively. Upper respiratory antibiotics are used in addition to a variety of vitamins, minerals and herbs to further combat the sore throat by introducing immunity building agents.

Experiments have been conducted and it was found that if a person gargles with this concentration of salt water heated to approximately 130 degrees Fahrenheit three (3) times a day at the onset of sore throat symptoms, consistently for a minimum of 3 days, they will not allow the infected cells to reproduce and ultimately, the number of bacterial cells drastically diminishes. Use of this therapeutic agent helped to treat and prevent sore throats, mouth sores and minor gum infections.

Another embodiment of a therapeutic rinse used to treat a bacterial sore throat has a liquid composition that includes about 7.5 mL of salt to about 180 mL of water to about 1 mg to about 20 mg of Zithromiacin brought to a temperature of about 130 degrees Fahrenheit. In certain embodiments, 5 mg, 10 mg, 15 mg and 20 mg of Zithromiacin is used in combination with the salt and water mixture. The temperature of the therapeutic rinse may range from about 100 degrees Fahrenheit to about 150 degrees Fahrenheit. Zithromiacin is an antibiotic used for treating upper respiratory infections. Although about 1 mg to about 20 mg of Zithromiacin is preferred, the amount of Zithromiacin may be about 1 mg to about 200 mg.

Normally antibiotics are used in the treatment of upper respiratory tract infections, which may include a sore throat. In most cases, if the upper respiratory tract infection is treated in its early stages with the antibiotic therapeutic rinse described above, water will move out of the bacterial cells and the antibiotic therapeutic rinse will be introduced to it thereby destroying the bacterial cells in its weakest state. In one experiment, gargling the antibiotic therapeutic liquid three (3) times a day, consistently for 3 days, destroyed a majority of the bacterial cells.

Antibiotics are the substances which kill or inhibit the growth of bacteria. The following antibiotics may be used in the liquid composition in addition to or in place of Zithormiacin: Azithromycin, Penicillin, cephalosporin, polymixin, quinolone, sulfonamides; Aminoglycoside, macrolide and tetracycline; cyclic lipopeptide (daptomycin), glycylcycline (tigecycline), and oxazolidinone (linezolid); Tigecycline, Erythromycin, Blephamide, Cefadroxil, Cefepime, Cefoxitin, cephalosporin, Cephazolin, cephalosporin, Chloramphenicol, Chlorsig, Clarithromycin, Clindamycin, Colistin, Dicloxacillin, Duricef, Floxin, Levaquin, Mefoxin, Minocycline, Norfloxacin, Omnicef, Pneumovax, Rifampin, Staphlex, Targocid, Tetracycline, Vancocin, Ambisome, Ampicillin, Bactroban, Cefaclor, Cefdinir, Cefixime, Cefpodoxime, Cephalexin, Ceptaz, Chloromycetin, Ciprofloxacin, Clindagel, Cloxacillin, Co-trimoxazole, Doxycycline, Erythromycin, Gatifloxacin, Levofloxacin, Meronem, Zymar, Cephradine, Cefotetan, Cefprozil, Loracarbef, Cefdinir, Cefoperazone, Cefotaxime, Ceftazidime, Ceftibuten, Ceftizoxime, Ceftriaxone, Ciprofloxacin, Gatifloxacin, Moxifloxacin, Ofloxacin, Ampicillin, Nafcillin, Penicillin VK, Piperacillin/tazobactam, Ticarcillin/clavulanate, Ampicillin/sulbactam, Amoxicillin/clavulanate, Penicillin G, Piperacillin, Ticarcillin, Doxycycline, Bacitracin, Mupirocin, Metronidazole, Aztreonam, Sulfa trimethoprim, Dapsone, Ertapenem, Imipenem, Meropenem, Metronidazole, Nitrofurantoin, Rifaximin, Tinidazole, Quincipristin, Dalfoprictin, Telithromycin, Sulfacetamide, Tazarotene, Amikacin, Gentamicin, Neomycin, Streptomycin, Tobramycin, Bacitracin, Mupirocin, Polymixin, and Silver sulfadiazine.

In another embodiment, a 6 oz. portion of the therapeutic rinse includes 7.5 mL (1½ Teaspoon) Dead Sea Salt, 5 mL (1 Teaspoon) Apple Cider Vinegar, 5 mL (1 Teaspoon) lemon concentrate, 1.25 mL (¼ Teaspoon) Cayenne Pepper, 2.5 mL (½ Teaspoon) Licorice Root, 112 mg (4 drops) Concentrated Oregano Oil, 5 mL (1 Teaspoon) Honey, and 10 mL of a blend of ingredients described below. In one embodiment, 0.07 mL of colloidal silver may also be included. Also, a preservative to allow shelf stability may be included in one embodiment. In one embodiment the 10 mL blend includes equal parts or zinc, slippery elm, Echinacea, B-complex, and valerian root. In another embodiment, the 10 mL blend may include equal parts of silver sulfadiazine, zinc, slippery elm, flavor enhancer, tumeric, and amino acids. A flavor enhancer, such as cherry or strawberry, may be used as desired in any of the described embodiments. These ingredients are mixed with water to create the 6 oz. portion of the therapeutic rinse. These concentrations can be scaled up or down to create 4 oz., 8 oz., 10 oz., 12 oz., or larger portions of the therapeutic rinse. Also, in other embodiments, the individual measurements of the listed ingredients may vary by 10%. Furthermore, all approximation given in this specification may vary by 10%.

In other embodiments, the 10 mL blend of ingredients can include any of the following vitamins, minerals, herbs and other ingredients: Amino Acids, Antioxidants, B Vitamins, C Vitamins, D Vitamins, Calcium, Enzymes, Garlic products, Bilberry, Black Cohosh, Cascara Sagrada, Cinnamon, Dandelion Root, Echinacea, Ginko Biloba, Ginseng complex, Green tea extract, Hawthorn Berries, Milk Thistle, Noni, Saw Palmetto, St. John's Wort, Super Guarana, Tumeric/Curcumin with Tumeric Extract, Valerian Root, Chromium Picolinate, Iron, Kelp, Magnesium, Potassium, Selenium, Zinc, Slippery Elm, Paprika, and/or natural and organic flavor enhancers as desired, and/or Colloidal Silver.

In yet another embodiment, the therapeutic rinse may even be in a spray or inhaler form. Also, the therapeutic rinse can be in tablet or powder form that can then be added to water (any temperature) for gargling and rinsing as described above. This embodiment will allow the user to choose the most convenient option with the liquid pouch that self-heats upon activation for prompt action/use regardless of whereabouts; and a more staple version in a tablet or powder form to always keep on hand at the home/office for use when the need arises. The tablets or powder will come in a typical plastic tube case, that may be biodegradable. The tablets or powder form will include salt, a variety of vitamins, minerals, herbs and an antibiotic. Both the tablet or powder form will be designed to dissolve in water to create a mixture for treating sore throats, mouth sores, minor gum infections or for use as a first aid disinfectant. In one embodiment, each tablet or tablespoon of powder will include about 5 mg to 20 mg of an antibiotic and may contain a flavor enhancer.

Timely use of the antibiotic therapeutic rinse may kill the bacterial and other germs before a more severe cold or sore throat develops. The embodiments of the therapeutic rinse described herein provide an effective method to kill bacteria versus current over-the-counter remedies that numb the throat region for temporary pain relief. Furthermore, the self-heating container serves as a convenient shelf stable product for a quick remedy that may be used anywhere, anytime immediately—for the unexpected onset of a sore throat symptom—at school, work, in route on business, on vacation, etc. Since the packaging offers a self-heating feature for a warm gargle, a more effective absorption rate occurs for best results. Also, the all-in-one packaging allows the user to be thorough and consistent in gargling three times a day regardless of a busy schedule. It is recommended that user activate the package for a quick heat, shake, gargle one package (includes up to five gargles) in the morning, repeat in the afternoon, and repeat in the evening post meals.

Disinfecting Rinse

In another embodiment, a disinfecting rinse is used to clean, disinfect and treat minor scrapes and abrasions to guard against bacterial infections. The disinfecting rinse can be used when other first aid kits or remedies are not available. This embodiment is intended as a portable emergency rinse that is convenient for school, travel, sports, workplace, and the like. The disinfecting rinse can include a cleaning embodiment and a treating embodiment.

One embodiment for a disinfecting rinse is a liquid composition that includes any type of soap or derivative of fatty acid and water that is brought to a temperature of about 130° F. Raising the temperature to about 130° F. provides improved results. However, the temperature of the disinfecting rinse may range from about 100° F. to about 150° F.

Another embodiment for the disinfecting rinse include a liquid composition including salt, water and an antibiotic powder. An intricate ratio of each element to prove both safe and effective in disinfecting and topically treating minor cuts or abrasions may be about 7.5 mL of salt to about 180 mL of water to about 1 mg to about 20 mg of Cephalexin. The ration may be about 15 mL of sodium chloride to about 79 mL of water in another embodiment. Cephalexin is an antibiotic typically used to treat bacterial infections of the skin. Although about 1 mg to about 20 mg of Cephalexin is preferred, the amount of Cephalexin may be about 1 mg to about 200 mg. It has also been contemplated that other antibiotics from the list described above can be included in place of or in addition to Cephalexin. This liquid composition is then brought to a temperature of about 130° F. However, the temperature of the disinfecting rinse may range from about 100° F. to about 150° F.

The disinfecting rinse provides a portable means to effectively clean, disinfect and treat minor cuts and abrasions, and guard against bacterial infection. The disinfecting rinse offers a shelf stable product to store in critical areas, such as a car, lockers, office, travel pack, and the like, so that it is available in the moment of need with no compromise to remedy.

Many antibiotic first-aid products contain combinations of antibiotics to make them effective against a broad range of bacteria. When treating a wound, it is not enough to simply apply a topical antibiotic. The wound must first be cleaned with soap and water and patted dry. Then, topical antibiotics help prevent infections caused by bacteria that get into minor cuts, scrapes, and burns. Treating minor wounds with antibiotics allows quicker healing. If the wounds are left untreated, the bacteria will multiply, causing pain, redness, swelling, itching, and oozing. Untreated infections can eventually spread and become much more serious.

Packaging:

As mentioned above, in one embodiment, the liquid composition of the therapeutic rinse and disinfecting rinse is packaged in a self-heating container, such as a pouch 10 (FIG. 1), flexible tube stick 20 (FIG. 2), bottle 30 (FIG. 3), or carton 40 (FIG. 4). The self-heating containers may have reservoirs for holding the rinse ranging from 4 oz., 6 oz., 8 oz., or larger in size. The containers may each have an activation zone or area such as a flexible wall, tab, or screw that when pressed, pulled, or turned by the user actives the self-heating container. The activation zone may be located anywhere on the self-heating container. By way of example and not by way of limitation, an activation portion 35 is shown near the bottom of the bottle 30 shown in FIG. 3. Once the package is activated, the package can self heat to a temperature of about 130° F. for a warm temperature rinse. An activated package can also be configured to reach temperatures of about 150° F. In use, the warm temperature of the liquid composition offers greater absorption. For a treatment, a user should shake the self-heating container to dissolve the salt and antibiotic powder in the water. The user may need to shake the self-heating container well before each gargle. In one embodiment, a cap 50 that screws on and off of the self-heating container 10, 20, 30 or 40 measures exactly one (1) Tablespoon of liquid that can be used for each gargle rinse. The self-heating container packaging may be biodegradable so that it is environmentally responsible.

Self-heating containers are known to those of ordinary skill in the art. Self-heating containers may include various mechanisms for creating an exothermic reaction by mixing various chemicals. In general, the self-heating container can be activated by the user using manual force. For instance, force can be applied to an activator located on the self-heating container, such as a moveable part or barrier. Once the activator is activated, mechanisms within the self-heating container allow chemicals to mix and react, allowing the temperature of the mixed concentration to increase, and thereby heating the contents in a reservoir of the self-heating container. Examples of self-heating containers are shown in U.S. Publication Nos. 2010/0224510 and 2009/0078711. Some self-heating containers are activated by adding water onto an ionic solid, such as calcium oxide or calcium chloride. Examples of this type may be found in U.S. Pat. No. 5,626,022 (Scudder et al.), U.S. Pat. No. 5,388,565 (Ou), and U.S. Pat. No. 4,773,389 (Hamasaki).

Self-heating containers may also include the mechanism of mixing acids and bases. An example of this type of self-heating container is U.S. Pat. No. 5,935,486 (Bell et al.) that involves mixing of various organic and inorganic acids and bases.

Another type of self-heating container uses oxidation-reduction reactions occurring in the aqueous phase. Examples of this type include U.S. Pat. No. 5,517,981 (Taub et al.) in which magnesium is mixed with cupric chloride in the presence of water and U.S. Pat. No. 3,998,749 (Hydro et al.) where aluminum and cupric chloride are mixed in a mixture of aqueous and organic solvents.

Yet another type of self-heating container uses solid phase self-propagating high-temperature synthesis (SHS) reactions, which include oxidation-reduction processes in the solid-state (such as thermite reactions). Examples include U.S. Pat. No. 4,506,654 (Zellweger et al.), U.S. Pat. No. 4,819,612 (Okamoto et al.), U.S. Pat. No. 4,949,702 (Suzuki et al.), U.S. Pat. No. 5,020,509 (Suzuki et al.), and U.S. Pat. No. 5,220,908 (Iizuna et al.). In all of these examples, the fuel is a mixture of a metal or alloys, such as silicon or ferrosilicon and a metal oxide, such as ferric oxide or cupric oxide. These reactions are basically redox reactions between metals or semimetals and metal oxide, such as aluminum, silicon and ferric oxide.

Any of these known types of self-heating containers may be used to heat the therapeutic rinse and/or disinfecting rinse. Furthermore, any new type of self-heating container may also be used with the above embodiments of the therapeutic rinse and/or disinfecting rinse.

Thus, it will be understood by those of skill in the art that changes may be made to the present invention, and that changes in its use may also be made, without departing from the spirit of the invention, which is defined in the following claims.

I claim:

1. A therapeutic rinse product for treating a sore throat, mouth sore and/or minor gum infection comprising:
   a self heating container having a reservoir, and the self heating container being capable of reaching a temperature of at least 130 degrees Fahrenheit when activated;
   a liquid composition including sodium chloride, vinegar, licorice root, honey, an antibiotic, and water stored in the reservoir of the self heating container;
   wherein the liquid composition is heated inside the self heating container upon activating the heating mechanism of the self heating container.

2. The product of claim 1, wherein the liquid composition includes about 7.5 mL sodium chloride, 5 mL vinegar, about 2.5 mL licorice root, and 5 mL honey.

3. The product of claim 2, wherein the liquid composition includes about 1.25 mL cayenne pepper, 5 mL lemon concentrate, and about 112 mg concentrated oregano oil.

4. The product of claim 3, wherein the liquid composition is about 6 ounces.

5. The product of claim 1, wherein the liquid composition includes a ratio of about 7.5 mL of sodium chloride to about 180 mL of water.

6. The product of claim 1, wherein the liquid composition includes a total of about 180 mL.

7. The product of claim 6, wherein the liquid composition includes about 1 mg to about 20 mg of antibiotic.

8. The product of claim 1, wherein the liquid composition includes zinc, flavor enhancer cherry flavor, slippery elm, Echinacea, B-complex, and valerian root.

9. The product of claim 1, wherein the liquid composition also includes the antibiotic selected from the group consisting of colloidal silver, Zithromiacin and cephalexin.

10. The product of claim 1, wherein the self heating container is a pouch.

11. The product of claim 1, wherein the self heating container is a flexible tube.

12. The product of claim 1, wherein the self heating container is a bottle.

13. The product of claim 1, wherein the self heating container is a container.

14. A therapeutic rinse product for treating a sore throat, mouth sore and/or minor gum infection comprising:
   a container including a reservoir; and
   a liquid composition including about 7.5 mL sodium chloride, about 5 mL vinegar, about 2.5 mL licorice root, about 5 mL honey, about 1.25 mL cayenne pepper, about 112 mg concentrated oregano oil, and water stored in the reservoir of the container.

15. The product of claim 14, wherein the liquid composition is about 6 ounces.

16. The product of claim 14, wherein the liquid composition includes zinc, slippery elm, Echinacea, B-complex, and valerian root.

17. The product of claim 14, wherein the container is a self heating container capable of reaching a temperature of at least 130 degrees Fahrenheit when activated.

18. A method of preparing a therapeutic rinse, the method comprising:
   preparing a liquid composition including sodium chloride, water, vitamins, minerals, herbs and an antibiotic, wherein a ratio of about 7.5 mL of sodium chloride to about 180 mL of water is used; and
   placing the liquid composition into a reservoir of a self heating container, wherein the self heating container is capable of reaching at least 130 degrees Fahrenheit.

19. The method of claim 18, wherein the liquid composition includes a total of about 180 mL.

20. The method of claim 18, wherein the liquid composition includes about 1 mg to about 20 mg of antibiotic.

* * * * *